United States Patent [19]

Baum

[11] Patent Number: 4,535,766
[45] Date of Patent: Aug. 20, 1985

[54] METHOD AND APPARATUS FOR MONITORING A RESPIRATOR USABLE WITH AN ENDOTRACHEAL TUBE

[75] Inventor: Marcel Baum, Vienna, Austria

[73] Assignee: Drägerwerk Aktiengesellschaft, Fed. Rep. of Germany

[21] Appl. No.: 463,644

[22] Filed: Feb. 3, 1983

[30] Foreign Application Priority Data

Feb. 23, 1982 [DE] Fed. Rep. of Germany ....... 3206482

[51] Int. Cl.³ ............................................ A61M 16/00
[52] U.S. Cl. ......................... 128/204.23; 128/202.22; 128/204.25
[58] Field of Search ..................... 128/200.21, 204.21, 128/204.23, 204.24, 204.25, 204.26, 205.24, 202.22

[56] References Cited

U.S. PATENT DOCUMENTS

| | | | |
|---|---|---|---|
| 3,730,180 | 5/1973 | Davison | 128/204.24 |
| 3,817,246 | 6/1974 | Weigl | 128/204.24 |
| 3,972,327 | 8/1976 | Ernst et al. | 128/204.21 |
| 3,976,065 | 8/1976 | Durkan | 128/204.24 |
| 4,030,492 | 6/1977 | Simbruner | 128/200.21 |
| 4,141,356 | 2/1979 | Smargiassi | 128/204.23 |
| 4,265,237 | 5/1981 | Schwanbom et al. | 128/205.24 |
| 4,270,530 | 6/1981 | Baum et al. | 128/204.25 |
| 4,318,399 | 3/1982 | Berndtsson | 128/204.23 |

FOREIGN PATENT DOCUMENTS 2063686  6/1981  United Kingdom ........... 128/204.25

Primary Examiner—Henry J. Recla
Attorney, Agent, or Firm—McGlew and Tuttle

[57] ABSTRACT

A method of safety monitoring a respirator which is connected to a patient through an endotracheal tube which has a respiratory gas jet nozzle delivering respiratory gas thereto and a measuring tube opening into the tube, comprising supplying at least one jet nozzle with a respiratory gas discharging into the tube, directing a fluid through the measuring tube at a substantially constant flow rate so that the variations in the pressure in the endotracheal tube will vary the pressure in the measuring tube, sensing the pressure in the measuring tube and controlling the flow through the jet nozzle in accordance with the pressure in the measuring tube, and wherein the flow of fluid in the measuring tube is set sufficiently low that in the event of a negligible pressure drop in the tube the pressure measured in the connection of the measuring tube at least approximately corresponds to the ambient pressure in the opening of the measuring tube.

10 Claims, 4 Drawing Figures

METHOD AND APPARATUS FOR MONITORING A RESPIRATOR USABLE WITH AN ENDOTRACHEAL TUBE

FIELD AND BACKGROUND OF THE INVENTION

The invention relates to a method of monitoring the safety of a respirator with an endotracheal tube, whereby at least one jet nozzle supplied by a respiratory gas source and a measuring tube terminate in the vicinity of the distal end of the tube, the measuring tube shutting off the respiratory gas source through a pressure sensor and a switch if the pressure exceeds a preset limit. In addition, a plurality of devices are provided in which the method can be worked advantageously.

Respirators which permit HFPPV (high frequency positive pressure ventilation) are known for respiration or assisting respiration. For example, according to German OS No. 28 47 681, an endotracheal tube is used for this purpose which has at its distal end two jet nozzles and one sampling tube supplied by a respiratory gas source at overpressure, by which the monitoring processes can be carried out.

The respiratory gas stream emerging from the jet nozzles has a driving pressure of 1-5 bars. The incoming volume of gas is largely independent of the impedance of the lungs. If the expiratory pathway (main lumen) becomes blocked above the jet oulet point, an inadmissibly high over pressure will develop in the bronchi in a relative short period of time (approximately 20 to 40 seconds). In general, this can cause rupturing and severe damage to the lungs. Blockage of the expiratory pathway can occur in various ways, for example, by accumulation of secretion or kinking of the endotracheal tube resulting in blockage of the expiratory pathway while gas continues to be supplied at high pressure.

To avoid these disadvantages, it is already known from German OS No. 28 34 037 to dispose a sampling or sensing tube in the air flow and monitor the pressure prevailing therein in this fashion. When an inadmissibly high overpressure is detected, the respiratory gas source is disconnected by an appropriate indirectly controlled switching mechanism. However, a design of this type offers no guarentee against kinking and/or plugging of the sampling or sensing tube, because in this case the normal pressure prevailing at a given moment will be stored, and the switching mechanism will not operate to shut off the respiratory gas flow despite and instant pressure rise in the airways.

SUMMARY OF THE INVENTION

The invention is based upon the idea of improving on a method of the type recited herein above such that kicking and/or shifting of the measuring tube can also be monitored. The respiratory gas composition in the vicinity of the jet nozzle outlet can also be monitored by a sampling tube. To achieve this goal, a provision is made such that the measuring tube carries a flow of a fluid with an at least approximately constant flowrate. The fluid emerges at the opening. The pressure in the measuring tube controls the respiratory gas source of the jet nozzle in such fashion that the respiratory gas source is shut off if the pressure of the fluid in the measuring tube exceeds a preset limit. The flow of the fluid is set sufficiently low that if there is a negligible pressure drop in the measuring tube, the pressure measured at the connection of the measuring tube will at least approximately correspond to the ambient pressure at the opening of the measuring tube (microflex). This method offers considerable additional security and monitors the potency of the measuring tube, because any kinking or blockage immediately causes a pressure rise in the fluid, which results in immediate shutoff of the respiratory gas source through an appropriate switching unit.

The fluid used in the measuring tube may be a liquid such as water, which may serve to humidify the respiratory gas emitted by the jet nozzle, or it may be a gas such as a respiratory gas.

Accordingly it is an object of the invention to provide an improved method for safety monitoring of respirator using a measuring tube.

A further object of the invention is to provide a respirator for use with an endotracheal tube which includes a measuring tube for measuring the pressure in the tube and for regulating the flow thereby.

A further object of the invention is to provide a respirator which is simple in design, rugged in construction and economical to manufacture.

The various features of novelty which characterize the invention are pointed out with particularity in the claims annexed to and forming a part of this disclosure. For better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
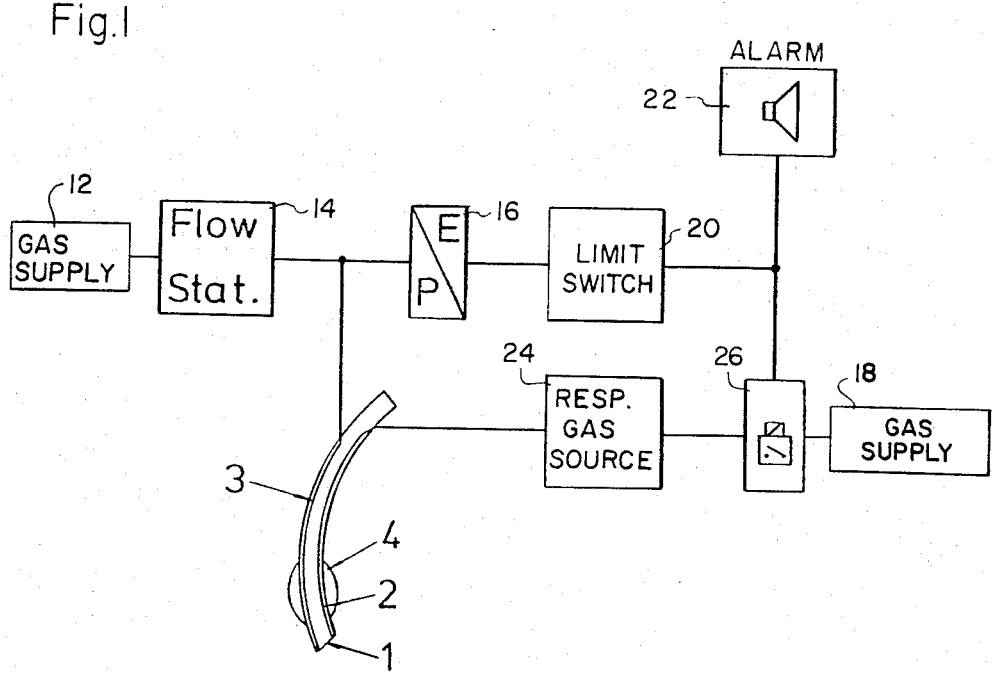
FIG. 1 is a block diagram illustrating a respirator constructed in accordance with the invention.

FIG. 1 shows an endotracheal tube 1, which includes a jet nozzle 2 supplied by a respiratory gas source and a measuring tube 3 embedded in the tube wall. An inflatable sealing cuff 4 is provided to hold the tube 3 and jet nozzle 2 in place.

A respiratory gas source 12 and a device or flow stat 14 are supplied from a central gas supply 12, producing an approximately constant microflow with a pressure of approximately 2 mbar through measuring tube 3 in the direction of the distal end of the tube.

The pressure in measuring tube 3 is monitored by a pressure sensor 16 with an electrical signal output. The electrical output signal triggers a control signal when a preset limit is exceeded in a limit switch 20, the signal activating an acoustic alarm 22 and shutting off a respiratory gas source 24 by a switch 26 connected to a gas supply 18.

Figure 2:
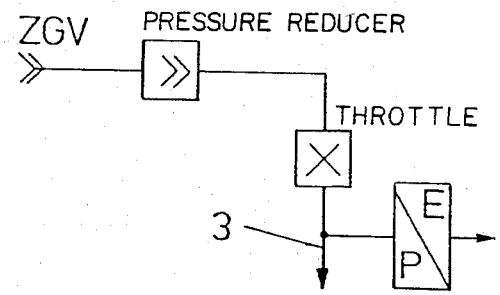
FIG. 2 is a view similar to FIG. 1 showing another embodiment of the invention.

In the device shown in FIG. 2, a pressure reducer and a throttle point are connected downstream of the central gas supply ZGV, producing a constant microflow. The pressure rise in the measuring tube is monitored by the pressure sensor E/P connected between the throttle point and the connection of measuring tube 3.

Figure 3:
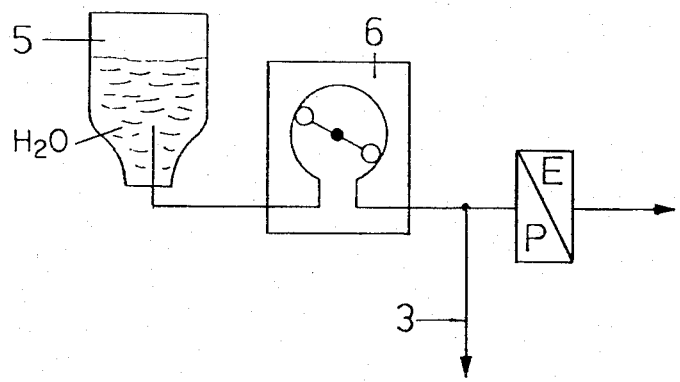
FIGS. 3 and 4 are views similar to FIG. 2 of still further embodiments of the invention.

The design shown in FIG. 3 uses water from a reservoir 5 to generate the microflow, said water being fed by a peristaltic pump 6 into the measuring tube 3.

Figure 4:
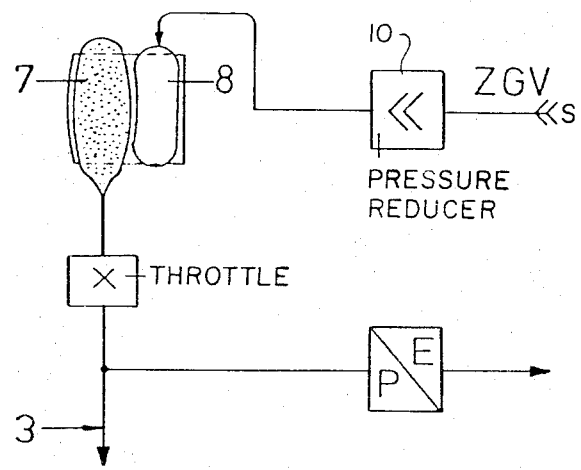

In the embodiment shown in FIG. 4, likewise using a liquid fluid, an elastic bag 7 filled with the fluid is provided, said bag being surrounded by a pressure cuff 8. Pressure cuff 8 is inflated by the central gas supply S (or ZGV) with the interposition of a pressure reducer 10, so that elastic bag 7 is emptied slowly.

With the method for monitoring the safety of a respirator used in the device, an endotracheal tube 1 comprising a jet nozzle 2 and a measuring tube 3 is used. The respirator is thereby protected against incorrect readings if measuring tube 3 is kinked or plugged, by virtue of the fact that a microflow of a fluid which emerges at the opening of measuring tube 3 flows through measuring tube 3. An inadmissible pressure rise in measuring tube 3 will shut off the respiratory gas source for jet nozzle 2.

It will be clear from the foregoing that the pressure reducer and throttle point, which are located downstream of the central gas supply ZGV for producing a constant microflow, per FIG. 2; the peristaltic pump 6, which is located downstream from the water reservoir 5, for generating the corresponding peristaltic microflow, per FIG. 3; and the throttle, located downstream from the liquid fluid filled elastic bag 7 surrounded by the pressure cuff 8 which is inflated by the central gas supply S or ZGV through the interposed pressure reducer 10 for emptying the liquid from the bag 7 slowly, per FIG. 4; all involve feed devices controllable for producing an at least approximately constant flow of the fluid to the measuring tube, with the corresponding pressure sensor being disposed between such feed device and the measuring tube connection.

It will also be clear from the foregoing that the ambient pressure in the endotracheal tube 1 consequent the delivery of the repiratory gas thereto via the jet nozzle 2 will inherently provide a reference pressure in the measuring tube 3, such that upon kinking or otherwise blockage of the measuring tube 3 the pressure therein will in turn at least approximately correspond to such ambient pressure or reference pressure and will increase under the substantially constant flow rate of the microflow of the fluid supplied thereto until the pressure exceeds the predetermined amount or limit at which the pressure sensor 16 is set for stopping the flow through the jet nozzle 2.

An example of a similar respirator is shown in application Ser. No. 378,386 filed May 14, 1982.

While specific embodiments of the invention have been shown and described in detail to illustrate the application of the principles of the invention, it will be understood that the invention may be embodied otherwise without departing from such principles.

What is claimed is:

1. Method of safety monitoring a respirator which is connected to a patient through an endotracheal tube which has at least one respiratory gas jet nozzle extending therein and terminating in a direction toward the distal end thereof for delivering respiratory gas thereto and a measuring tube terminating in an opening which opens into the endotracheal tube, which comprises supplying the at least one jet nozzle with a flow of a respiratory gas discharging into the endotracheal tube, supplying a flow of fluid to the measuring tube at a substantially constant flow rate for discharge from the opening into the endotracheal tube and such that variations in the ambient pressure in the endotracheal tube will vary the pressure in the measuring tube, directly sensing the amount of pressure in the measuring tube and stopping the flow through the at least one jet nozzle to the endotracheal tube when the pressure sensed in the measuring tube exceeds a predetermined amount, the flow of fluid in the measuring tube being set sufficiently low such that in the event of a negligible pressure drop in the measuring tube the amount of pressure sensed in the measuring tube at least approximately corresponds to the ambient pressure at the opening of the measuring tube and such that in the event of a kinking or otherwise blockage of the measuring tube the pressure therein will in turn at least approximately correspond to such ambient pressure and will increase under the substantially constant flow rate of the flow of fluid supplied thereto until the pressure sensed exceeds the predetermined amount for stopping the flow through the at least one jet nozzle.

2. Method of claim 1 wherein the fluid supplied for flow through the measuring tube is a liquid fluid.

3. Method of claim 1 wherein the fluid supplied for flow through the measuring tube is a liquid fluid such as water and serves to humidify the respiratory gas emitted by the at least one jet nozzle.

4. Method of claim 1 wherein the fluid supplied for flow through the measuring tube is a respiratory gas component.

5. Method of safety monitoring a respirator which is connected to a patient through an endotracheal tube which has at least one respiratory gas jet nozzle extending therein and terminating in a direction toward the distal end thereof for delivering respiratory gas thereto and a measuring tube terminating in an opening which opens into the endotracheal tube, which comrpises supplying the at least one jet nozzle with a flow of a respiratory gas discharging into the endotracheal tube and thereby providing a corresponding ambient pressure in the endotracheal tube, supplying a flow of fluid to the measuring tube at a substantially constant flow rate as a microflow for discharge from the opening into the endotracheal tube and such that variations in the ambient pressure in the endotracheal tube will vary the pressure in the measuring tube, directly sensing the amount of pressure in the measuring tube, the flow of fluid in the measuring tube being set sufficiently low such that in the event of a negligible pressure drop in the measuring tube the amount of pressure sensed in the measuring tube at least approximately corresponds to the ambient pressure at the opening of the measuring tube, said ambient pressure thereby providing a reference pressure in the measuring tube and such that in the event of a kinking or otherwise blockage of the measuring tube the pressure therein will in turn at least approximately correspond to such ambient pressure and will increase under the substantially constant flow rate of the fluid supplied thereto until the pressure sensed exceeds a predetermined amount, and stopping the flow through the at least one jet nozzle to the endotracheal tube when the pressure sensed in the measuring tube exceeds the predetermined amount.

6. Respirator for use with an endotracheal tube, comprising an endotracheal tube having an interior remote end insertable in a person's trachea, a measuring tube connected into the endotracheal tube and termination in an opening at the interior remote end thereof, at least one jet nozzle for respiratory gas connected into said endotracheal tube in the interior thereof adjacent the remote end thereof for discharging respiratory gas into the endotracheal tube for thereby providing a corresponding ambient pressure in the endotracheal tube, a fluid source having a flow control and connected to said measuring tube for supplying a fluid to said measuring tube set at a substantially constant flow rate, a respiratory gas supply having a regulatory switch connected to said at least one jet nozzle and pressure sensor means connected to said measuring tube for directly measuring pressure therein, means responsive to said pressure sensing means and connected to said regulatory switch and effective to shut off the flow of said at least one jet nozzle at a predetermined value of the sensed pressure in said measuring tube, said predetermined value exceeding the corresponding ambient pressure provided by the respiratory gas discharging from said at least one jet nozzle into the endotracheal tube such that in the event of a kinking or otherwise blockage of said measuring tube the pressure therein will in turn at least approximately correspond to such ambient pressure and will increase under the substantially constant flow rate of the fluid supplied thereto until the pressure sensed exceeds said predetermined amount for shutting off the flow of said at least one jet nozzle.

7. Respirator of claim 6 wherein said pressure sensor means is located between said flow control of said fluid source and the connection of said measuring tube thereto.

8. Respirator of claim 5 wherein said fluid source includes a pressure valve and a throttle connecting said fluid source to said measuring tube, said pressure sensor means being disposed between the connection of said measuring tube and said throttle.

9. Respirator of claim 4 wherein said fluid source includes a reservoir for liquid fluid connected to said measuring tube, and a pump disposed between said reservoir and said measuring tube, said pressure sensor means being disposed between said pump and the connection of said measuring tube.

10. Respirator of claim 7 wherein said fluid source includes an elastic bag containing a liquid fluid, an inflatable cuff surrounding said elastic bag and being inflatable by an auxiliary gas source, said bag having an outlet connected to said measuring tube through a throttle point, said pressure sensor means being disposed between said throttle point and the connection of said measuring tube.

* * * * *